United States Patent
Shi et al.

(10) Patent No.: US 9,045,322 B2
(45) Date of Patent: Jun. 2, 2015

(54) CAP STERILIZING MECHANISM FOR BOTTLE FILLING DEVICE

(75) Inventors: Zheng Shi, Zhejiang (CN); Yonglin Ji, Zhejiang (CN); Zhengfa Wang, Zhejiang (CN)

(73) Assignee: HANGZHOU ZHONGYA MACHINERY CO., LTD., Hangzhou (CN)

( * ) Notice: Subject to any disclaimer, the term of this patent is extended or adjusted under 35 U.S.C. 154(b) by 616 days.

(21) Appl. No.: 13/395,278

(22) PCT Filed: Dec. 31, 2009

(86) PCT No.: PCT/CN2009/076383
§ 371 (c)(1),
(2), (4) Date: Mar. 9, 2012

(87) PCT Pub. No.: WO2011/029259
PCT Pub. Date: Mar. 17, 2011

(65) Prior Publication Data
US 2012/0183451 A1    Jul. 19, 2012

(30) Foreign Application Priority Data
Sep. 10, 2009    (CN) .......................... 2009 1 0102267

(51) Int. Cl.
| | |
|---|---|
| *A61L 2/00* | (2006.01) |
| *A61L 9/00* | (2006.01) |
| *B67B 3/00* | (2006.01) |
| *A61L 2/16* | (2006.01) |
| *A61L 2/22* | (2006.01) |
| *A61L 2/18* | (2006.01) |

(52) U.S. Cl.
CPC . *B67B 3/003* (2013.01); *A61L 2/16* (2013.01); *A61L 2/22* (2013.01); *A61L 2/18* (2013.01); *A61L 2/00* (2013.01)

(58) Field of Classification Search
CPC ............... A61L 2/22; A61L 2/16; A61L 2/18; A61L 2/20; B67B 3/003
USPC .......................... 422/302, 292, 295, 297, 300
See application file for complete search history.

(56) References Cited

U.S. PATENT DOCUMENTS

| | | | | |
|---|---|---|---|---|
| 2,043,411 | A | * | 6/1936 | Kimball .......................... 53/505 |
| 2,893,536 | A | * | 7/1959 | Jones .......................... 198/484.1 |
| 3,101,995 | A | * | 8/1963 | Beauvais ...................... 422/297 |
| 3,473,934 | A | * | 10/1969 | Pech ............................. 426/407 |

(Continued)

FOREIGN PATENT DOCUMENTS

| | | |
|---|---|---|
| CN | 1180324 A | 4/1998 |
| CN | 1837020 A | 9/2006 |

(Continued)

*Primary Examiner* — Regina M Yoo
(74) *Attorney, Agent, or Firm* — Birch, Stewart, Kolasch & Birch, LLP

(57) ABSTRACT

A cover sterilizing mechanism for bottle filling device includes a sterilizing chamber (II) in which a cover sliding passage (102) is arranged. A cover blocking mechanism which will periodically hold the cover (94) to stay on the sliding passage (102) for a certain time, and multiple groups of nozzles (62) corresponding to the place in which the cover (94) is held on the sliding passage(102) are also arranged in the sterilizing chamber (II). The cover sterilizing device can uniform the sterilizing time of each cover, conduce to install covers orderly and improve efficiency of the bottle filling device.

13 Claims, 2 Drawing Sheets

(56) References Cited

U.S. PATENT DOCUMENTS

| | | | | |
|---|---|---|---|---|
| 3,478,677 A | * | 11/1969 | Mencacci | 99/360 |
| 3,536,225 A | * | 10/1970 | Pech | 220/8 |
| 3,833,339 A | * | 9/1974 | Pacilio | 422/105 |
| 3,905,317 A | * | 9/1975 | Pacilio | 215/200 |
| 3,946,950 A | * | 3/1976 | Graf | 241/18 |
| 4,082,177 A | * | 4/1978 | Aidlin et al. | 198/453 |
| 4,449,050 A | * | 5/1984 | Kamhi | 250/455.11 |
| 4,661,325 A | * | 4/1987 | Noro et al. | 422/304 |
| 4,677,283 A | * | 6/1987 | Lewis | 235/98 C |
| 5,236,077 A | * | 8/1993 | Hoppmann et al. | 198/380 |
| 5,538,562 A | * | 7/1996 | Misaki | 134/6 |
| 5,673,783 A | * | 10/1997 | Radant et al. | 198/418.6 |
| 5,860,648 A | * | 1/1999 | Petermeier et al. | 273/108.2 |
| 6,206,171 B1 | * | 3/2001 | Crawford | 198/396 |
| 6,351,924 B1 | | 3/2002 | Gustafsson et al. | |
| 6,491,296 B2 | * | 12/2002 | Kelly et al. | 273/118 A |
| 6,588,363 B1 | * | 7/2003 | Burke et al. | 118/13 |
| 6,799,413 B2 | * | 10/2004 | Aylward | 53/473 |
| 7,005,455 B2 | * | 2/2006 | Cnossen et al. | 518/700 |
| 2004/0011623 A1 | * | 1/2004 | Sala | 198/373 |
| 2005/0279228 A1 | * | 12/2005 | Julian et al. | 99/537 |
| 2009/0077930 A1 | * | 3/2009 | Buchhauser et al. | 53/426 |
| 2010/0115892 A1 | * | 5/2010 | Aylward et al. | 53/473 |

FOREIGN PATENT DOCUMENTS

| | | |
|---|---|---|
| CN | 101371926 A | 2/2009 |
| CN | 101658685 A | 3/2010 |
| DE | 199 09 826 A1 | 9/2000 |
| EP | 0 824 974 A1 | 2/1998 |

* cited by examiner

CAP STERILIZING MECHANISM FOR BOTTLE FILLING DEVICE

FIELD OF THE INVENTION

The present invention relates to a cap sterilizing mechanism for a linear type bottle filling device.

BACKGROUND OF THE INVENTION

For the purpose of higher production efficiency of a linear type bottle filling device used to fill milk and milk beverages, bottles are normally arranged in a line, where filling, capping and cap tightening are conducted simultaneously. In this case, plastic caps after arrangement are required to be secondarily distributed to their corresponding slideways in an even manner After being sterilized, the plastic caps are precisely put on bottle openings subject to the predetermined requirements in order to facilitate the following tightening process. Conventionally, bottle caps are branched in the manner that the number of passageways increases geometrically, in other words, one passageway branches into two passageways, two into four, four into eight and the like. The capping is achieved by a power-free cap grabbing, more specifically, the bottle caps sliding off the preset slideways are blocked by two leaf springs at the front end of a grabbing head when the bottle caps are in an inclined state. As the front edge of a bottle cap is lower than the level of the bottle opening while the rear edge is higher than said level. When the bottles horizontally pass through the cap grabbing head, the bottle openings grab the front edges of the bottle caps, which are then carried away and fall on the bottle openings, during which the leaf springs block the following cap.

The aforesaid solution has the disadvantages that: 1. As the cap passageways increase geometrically, this will bring about huge-sized passageways in case of a great number of bottles are in the line; 2. The bottle caps are not blocked when passing through a sterilizing chamber, therefore the bottle caps are arranged all over the cap slideways. It is no problem for sterilization during normal working process but unfavorable for the beginning. When the bottle caps pass though the cap slideways rapidly due to less bottle caps distributed therein, consequently, the sterilizing is incomplete, the hygienic quality of the final products will be affected; 3. When grabbing is used for capping, if the bottle caps fail to precisely fit with the bottle openings, the bottle caps would not be covered properly. It will affect the following tightening effects. Furthermore, the grabbing head is disposed with the leaf springs for plastic caps, it is sometimes unreliable that the following cap may be carried over together with the previous one.

SUMMARY OF THE INVENTION

In view of the abovementioned problems, it is one object of the invention to overcome the drawbacks of the prior art by providing a cap sterilizing mechanism featuring complete sterilization for a linear type bottle filling device.

To achieve aforesaid object, the adopted technical solution is described below:

A cap sterilizing mechanism for a linear type bottle filling device, in accordance with the present invention, comprises a sterilizing chamber, in which a chamber body is disposed with a row of cap slideways extending downwards, a cap blocking mechanism is disposed to periodically block and hold caps standing in sequence on the cap slideways for a certain time, a plurality groups of nozzles are also disposed to face a section of the cap slideways where the caps are held still. When the technical solution provided herein is adopted, the sterilizing time for each cap is uniform, therefore the working quality of the linear type bottle filling device is improved.

DETAILED DESCRIPTION OF THE EMBODIMENTS

As shown in attached drawings, a cap sterilizing mechanism for a linear type bottle filling device, in accordance with the present invention, comprises a sterilizing chamber II, in which a chamber body is disposed with a row of cap slideways 102 extending downwards, a cap blocking mechanism is disposed to periodically block and hold caps standing in sequence on the cap slideways for a certain time, a plurality groups of nozzles are also disposed to face a section of the cap slideways where the caps are held still. The number of the cap slideways equals to that of bottle lines within the bottle filling device.

Figures 1, 2:
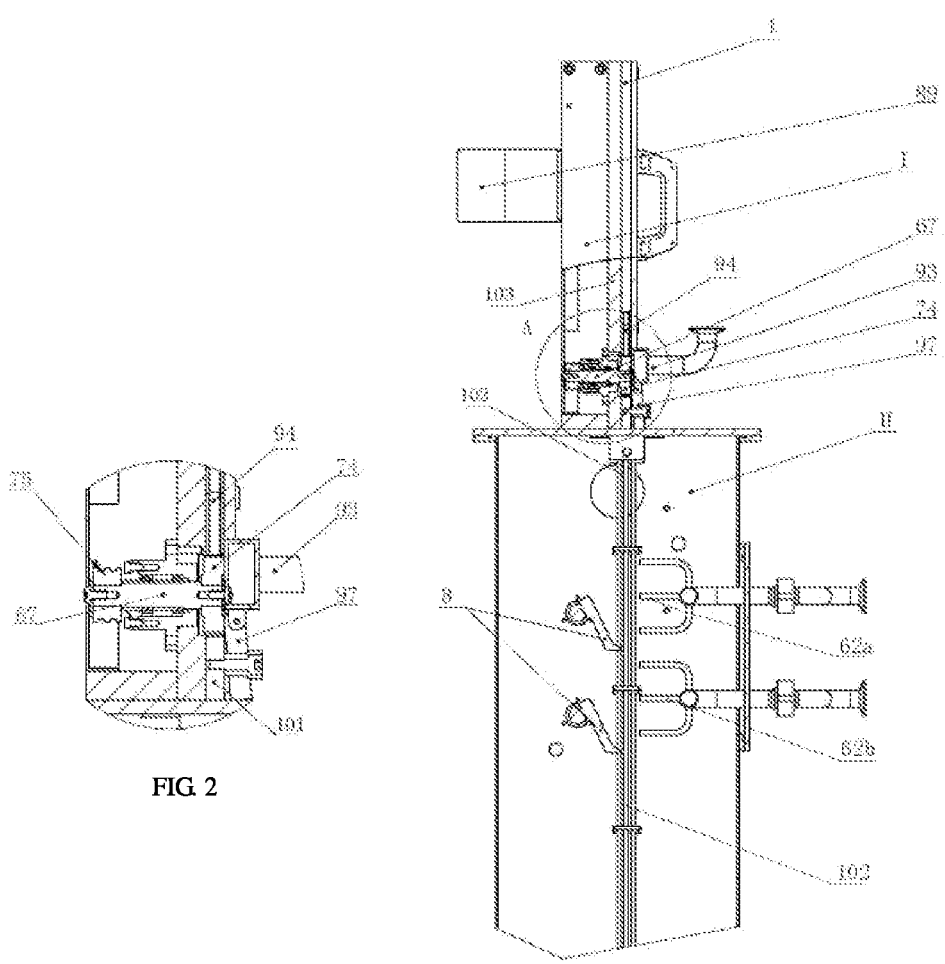
FIG. 1 is a partially side view of a cap sterilizing mechanism for a linear type bottle filling device in accordance with an example of the present invention.
FIG. 2 is an enlarged view of Portion A of FIG. 1 of the present invention.

As shown in FIG. 1, said cap slideways are disposed with sections which extend vertically downwards. The cap blocking mechanism is disposed facing such sections so that the caps can be held on these sections. Lower ends of the sections extending vertically downwards are further disposed with arc-shaped transition cap slideways bending downwards to connect with a capping apparatus. In this way, the sterilized caps slide under the gravity to the capping apparatus and then are put onto bottles.

Cap blocking functional pieces within the cap blocking mechanism provided in this example swing to periodically block the caps. Alternatively, said cap blocking functional pieces can also move circularly or linearly. The cap blocking functional pieces in a swinging motion are cap blocking claws 8 which block and hold the caps to stay on the cap slideways. As shown in the attached drawings, at least two rows of the swingable cap blocking claws 8 are disposed in the cap sliding direction within the cap blocking mechanism to form two cap parking sections on vertical sections of the cap slideways.

Figure 3:
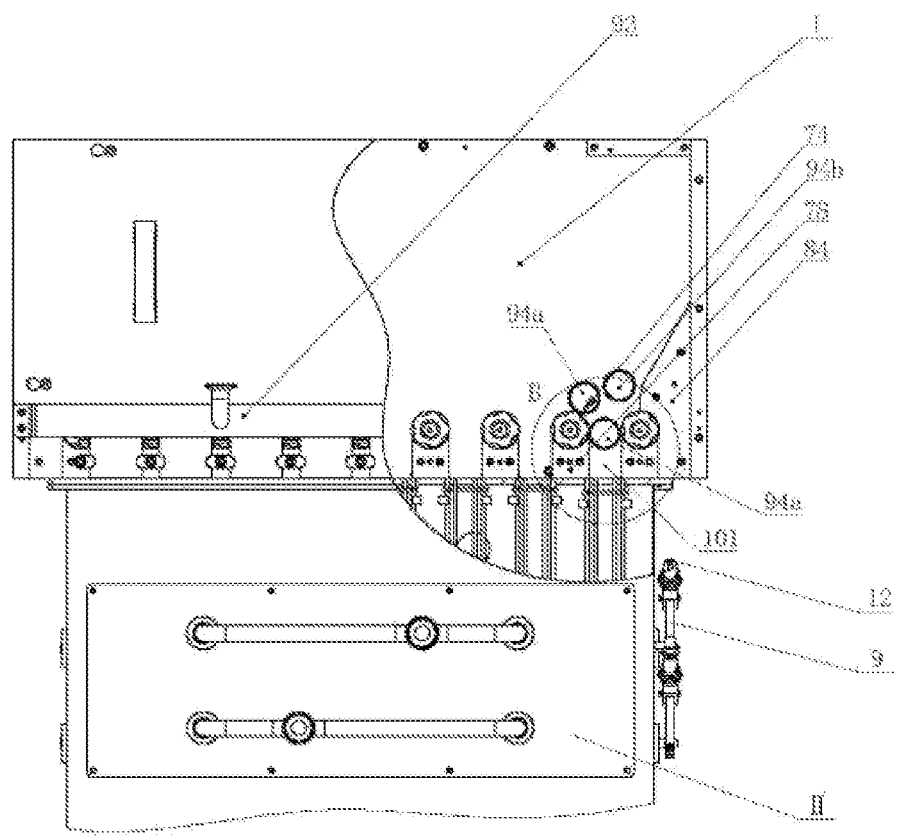
FIG. 3 is a partially sectional view of FIG. 1 of the present invention viewed from the right.

As shown in FIG. 3, a cylinder for driving the cap blocking claws to swing is numbered 12 and a drive mechanism is numbered 9.

The swinging of the cap blocking claws coincides with the transportation of the bottles which are transported by the bottle filling device to capping positions, more specifically, when one bottle is transported to the capping position by the bottle filling device, the cap blocking claws also act once to let one cap pass through. In this manner, uniform sterilization and smooth capping are achieved by avoiding jammed caps in the cap slideways.

As shown in the attached drawings, the cap slideways 102 are assembled from a plurality of bar profiles and have a hollowed groove bottom facilitating the cooperation between the cap blocking claws and the cap slideways to block the caps. In addition, positions where the cap blocking claws are inserted into the cap slideways depart from the cap slideway center, in other words, the cap blocking claws are inserted into the cap slideways via a clearance at the non-central portion formed between two adjacent caps by radians.

The nozzles include a nozzle 62a connecting sterilizing agent pipes and a nozzle 62b connecting sterilized hot air ducts, in which the nozzle 62a is located above the nozzle 62b. Upper ends of the cap slideways 102 are connected to cap outlet passages 101 of cap distributing apparatuses one to one. The cap distributing apparatuses includes a cap storage chamber 1 which is located within a cabinet I. Lower portion of the cap storage chamber is disposed with a row of cap outlets which let out the caps as many as the bottle lines. The cap outlets are designed to let out only one cap 94 for each time. Inside the cap storage chamber, cap shifters are disposed above the cap outlets.

By stirring or shaking the caps 94, the cap shifters timely separate or shake away other caps which have unfavorable effects on the caps in preferential positions directing to the cap outlets, consequently, jammed cap outlets 101 due to cross-affected caps are avoided and the caps orderly slide out of the cap outlets under the gravity one by one.

The cap shifter is a device capable of stirring or shaking the caps. In accordance with this example, cap shifter wheels 74 as a part of the cap shifters function to shift the caps, therefore, the cap shifters are simple in structure and easy to rotate. Meanwhile, the cap shifter wheels can be conveniently added based on different cap distribution needs for the bottle filling devices with varied production capacities. As shown in FIG. 3, the cap shifter wheels 74 are located at the left and right sides of the cap outlets, at the left side and the right side of each cap outlet are respectively provided with a cap shifter wheel. On the surface of the cap shifter wheels are circumferentially disposed with friction threads or a groove 740, allowing better shaking or stirring effects under the friction.

The cap storage chamber is an irregular cap storage space. The division plates 103 are disposed within the cabinet I to form the cap storage chamber, whose thickness is equal to the cap height. In other words, the caps enter into the cap storage chamber and then leave it from the cap outlets as shown in FIG. 1. As the thickness of the cap storage chamber is equal to or a little more than the cap height, only one cap can slide through its thickness direction at one time, therefore it is helpful for the cap shifters to function well and reduce their work difficulties, and meanwhile it is also helpful to prevent the jammed cap outlets. The rotation axis of the cap shifter wheels is perpendicular to a plane determined by both the length direction and the height direction of the cap storage chamber. The thickness refers to a horizontal width of the cap storage space shown in FIG. 1, the length direction refers to a horizontal direction of the cap storage chamber shown in FIG. 3 and the height direction refers to a direction from top to bottom shown in FIG. 1.

Figure 4:
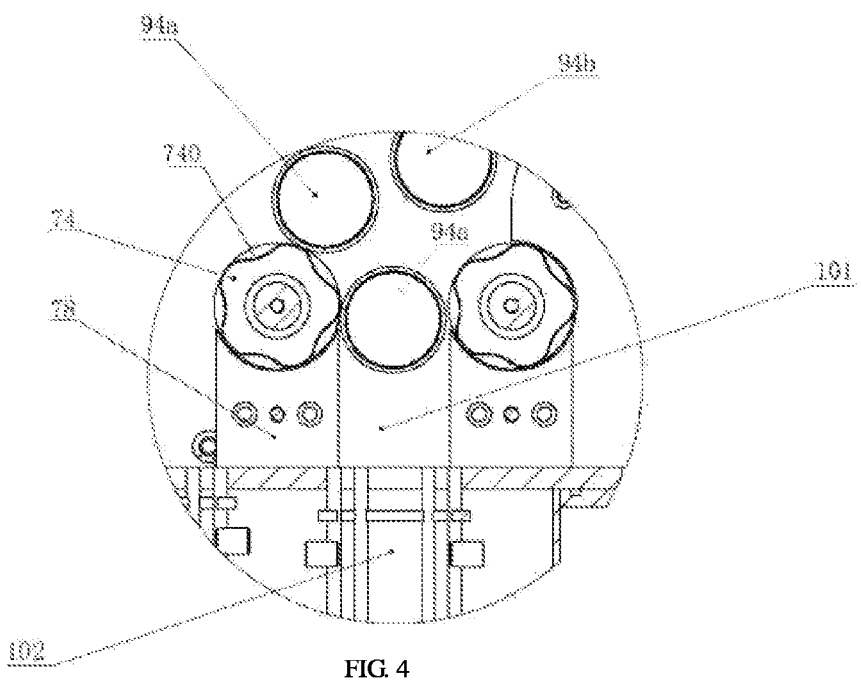
FIG. 4 is an enlarged view of Portion B of FIG. 3 of the present invention.

As shown in FIG. 4, the distance between the two cap shifter wheels which are respectively disposed at the left and right sides of the cap outlets is equal to or a litter more than a cap diameter, so that only one cap slides out of each cap outlet at one time.

The cap outlets extend to form cap outlet passages 102, which start bending downwards from an entrance between the cap shifter wheels respectively at left and right sides of the cap outlets. A blocking plate 78 under the cap shifter wheels defines boundaries of the cap outlet passages. At the both sides of the cap storage chamber are disposed with guide side plates 84.

The cap sterilizing mechanism provided herein also includes air shield pipes 93, which are connected with the sterilized air ducts and disposed with a plurality of fine vents. Each group of such vents separately faces the cap outlet passages from the lateral side. Sterilized air ejected from the air shield pipes 93 forms a sterilized air shield, such sterilized air shield stops the atomized sterilizing agent escaping from the sterilizing chamber II, where the cap slideways 102 is located and meanwhile stops the outside unsterilized air entering into the sterilizing chamber.

On the cap outlet passage side is disposed with a movable inspection door 97 which can be opened for clearing up when the cap outlets are obstructed.

As shown in FIGS. 1 and 3, the air shield pipes are located outside one side of the cap storage chamber, the movable inspection door is located at the side where the air shield pipes locate, and a drive device driving the cap shifter wheels to rotate is disposed at the other side of the cap storage chamber within the cabinet I. Such drive device is a belt drive device or a chain drive device which is disposed with a plurality of pulleys or chain wheels 75. A shaft 67 of the cap shifter wheels is coaxial with the pulleys or chain wheels.

During operations, plastic caps transported by cap arrangement devices enter into the cap storage chamber 1. When the drive device is driven by a motor 89, the cap shifter wheels 74 rotate in the same direction (the cap shifter wheels are assumed to rotate clockwise), so that the plastic caps shake in an irregular manner. As shown in FIG. 4, when both cap 94a and cap 94b reach to the cap outlets, the cap 94a is at the left side. Because the cap shifter wheels rotate clockwise, the cap 94a at the left side is located in a preferential position and carried by the cap shifter wheel at the left side into the cap outlet passages, and meanwhile the cap 94b at the right side are stirred to separate from the cap outlets. As a result obstructed cap outlet passages due to mutual impact between the cap 94a and the cap 94b are avoided.

To begin with the works, an upper row of cap blocking claws retract to block the plastic caps, which are then sterilized by the atomized sterilizing agent ejected from the nozzles. After that, a lower row of cap blocking claws retract while the upper row of cap blocking claws release, so that the bottle caps slide along the cap slideways to the lower row of the cap blocking claws and then the bottle caps are blocked. The bottle caps are dried by sterilized hot air ejected from the nozzles, in this way, sterilizing agent residue is removed. Then the lower row of the cap blocking claws release, the bottle caps slide along the cap slideways and the arc-shaped transition cap slideways bending downwards, finally the bottle caps reach to the capping apparatus. The above procedures are carried out repeatedly until the cap slideways are full of bottle caps, and then the capping process get started. In the following course, the upper and lower rows of cap blocking claws, based on the same procedures as described above, act in coincidence with the transportation of the bottles which are transported by the bottle filling device to the capping positions.

The invention claimed is:

1. A cap sterilizing mechanism for a linear type bottle filling device which comprises,
   a sterilizing chamber having a chamber body containing a row of cap slideways, extending downwards, said cap slideways having a hollowed groove bottom,
   a cap blocking mechanism disposed to periodically block and hold caps standing in sequence on the cap slideways for a certain time, said cap blocking mechanism containing swingable cap blocking claws which function to block and hold the caps standing on the cap slideways, and
   a plurality of nozzles disposed to face a section of the cap slideways where the caps are held still.

2. The cap sterilizing mechanism for the linear type bottle filling device according to claim 1, wherein the cap slideways contain sections extending vertically downwards, said sections being in further communication with said cap blocking mechanism.

3. The cap sterilizing mechanism for the linear type bottle filling device according to claim 2, wherein said cap blocking mechanism meets said sections extending vertically downwards to have at least two parking sections in the cap sliding direction.

4. The cap sterilizing mechanism for the linear type bottle filling device according to claim 3, wherein said nozzles include nozzle connecting sterilizing agent pipes and nozzle connecting sterilized hot air ducts, in which the nozzle connecting the sterilizing agent pipes is located above the nozzle connecting the sterilized hot air ducts.

5. The cap sterilizing mechanism for the linear type bottle filling device according to claim 2, wherein said nozzles include nozzle connecting sterilizing agent pipes and nozzle connecting sterilized hot air ducts, in which the nozzle connecting the sterilizing agent pipes is located above the nozzle connecting the sterilized hot air ducts.

6. The cap sterilizing mechanism for the linear type bottle filling device according to claim 1, wherein upper ends of said cap slideways are connected to cap outlet passages of cap distributing apparatuses, one to one; said cap sterilizing mechanism also including air shield pipes which are connected with sterilized air ducts, and vents on the air shield pipes separately face said cap outlet passages from the side.

7. A cap sterilizing mechanism for a linear type bottle filling device which comprises,
   a sterilizing chamber having a chamber body containing a row of cap slideways, extending downwards, said cap slideways having a hollowed groove bottom,
   a cap blocking mechanism disposed to periodically block and hold caps standing in sequence on the cap slideways for a certain time, said cap blocking mechanism containing at least two rows of swingable cap blocking claws disposed in the cap sliding direction within the cap blocking mechanism and functioning to block and hold the caps standing on the cap slideways, and
   a plurality of nozzles disposed to face a section of the cap slideways, where the caps are held still.

8. A cap sterilizing mechanism for a linear type bottle filling device which comprises,
   a sterilizing chamber having a chamber body containing a row of cap slideways extending downwards, wherein lower ends of said cap slideways are provided with a section of arc-shaped transition, cap slideways, bending downwards,
   a cap blocking mechanism disposed to periodically block and hold caps standing in sequence on the cap slideways for a certain time, and
   a plurality of nozzles disposed to face a section of the cap slideways, where the caps are held still.

9. The cap sterilizing mechanism for the linear type bottle filling device according to claim 8, wherein in the cap blocking mechanism contains swingable cap blocking claws which function to block and hold the caps standing on the cap slideways.

10. The cap sterilizing mechanism for the linear type bottle filling device according to claim 9, wherein at least two rows of the swingable cap blocking claws are disposed in the cap sliding direction within the cap blocking mechanism.

11. The cap sterilizing mechanism for the linear type bottle filling device according to claim 10, wherein the swinging of the cap blocking claws cooperates with the transportation of the bottles which are transported by the bottle filling device to capping positions.

12. The cap sterilizing mechanism for the linear type bottle filling device according to claim 9, wherein the swinging of the cap blocking claws cooperates with the transportation of the bottles, which are transported by the bottle filling device to capping positions.

13. The cap sterilizing mechanism for the linear type bottle filling device according to claim 9, wherein the cap slideways has a hollowed groove bottom.

* * * * *